United States Patent [19]

Robinson

[11] 4,311,133
[45] Jan. 19, 1982

[54] INTRA-AORTIC BALLOON

[75] Inventor: Thomas C. Robinson, Berkeley, Calif.

[73] Assignee: Thoratec Laboratories Corporation, Berkeley, Calif.

[21] Appl. No.: 128,580

[22] Filed: Mar. 10, 1980

[51] Int. Cl.³ .............................................. A61B 19/00
[52] U.S. Cl. ..................................................... 128/1 D
[58] Field of Search ............... 128/1 D, 349 R, 419 P; 46/156

[56] References Cited

U.S. PATENT DOCUMENTS

| | | | |
|---|---|---|---|
| 2,437,542 | 3/1948 | Krippendorf | 128/349 R X |
| 3,550,162 | 12/1970 | Huffman | 128/1 D X |
| 3,719,737 | 3/1973 | Vaillancourt | 128/349 R X |
| 3,769,960 | 11/1973 | Robinson | 128/1 D |
| 4,077,394 | 3/1978 | McCurdy | 128/1 D |

FOREIGN PATENT DOCUMENTS 321529 10/1959 United Kingdom ................. 46/156

Primary Examiner—Harland S. Skogquist
Attorney, Agent, or Firm—Lothrop & West

[57] ABSTRACT

An intra-aortic balloon includes a flexible catheter having a deformable fitting closing one terminus and a connecting attachment at the other end. Adjacent the fitting, the catheter has a number of perforations all within an elongated balloon surrounding the perforations. One end of the balloon is secured to the fitting and at the other end is secured to the catheter. The connecting attachment is engageable with a removable body to which is secured a manually deformable wire extending through the catheter and into the fitting. The body has a duct open to the interior of the catheter and to the atmosphere. An outwardly opening check valve is in the duct.

4 Claims, 5 Drawing Figures

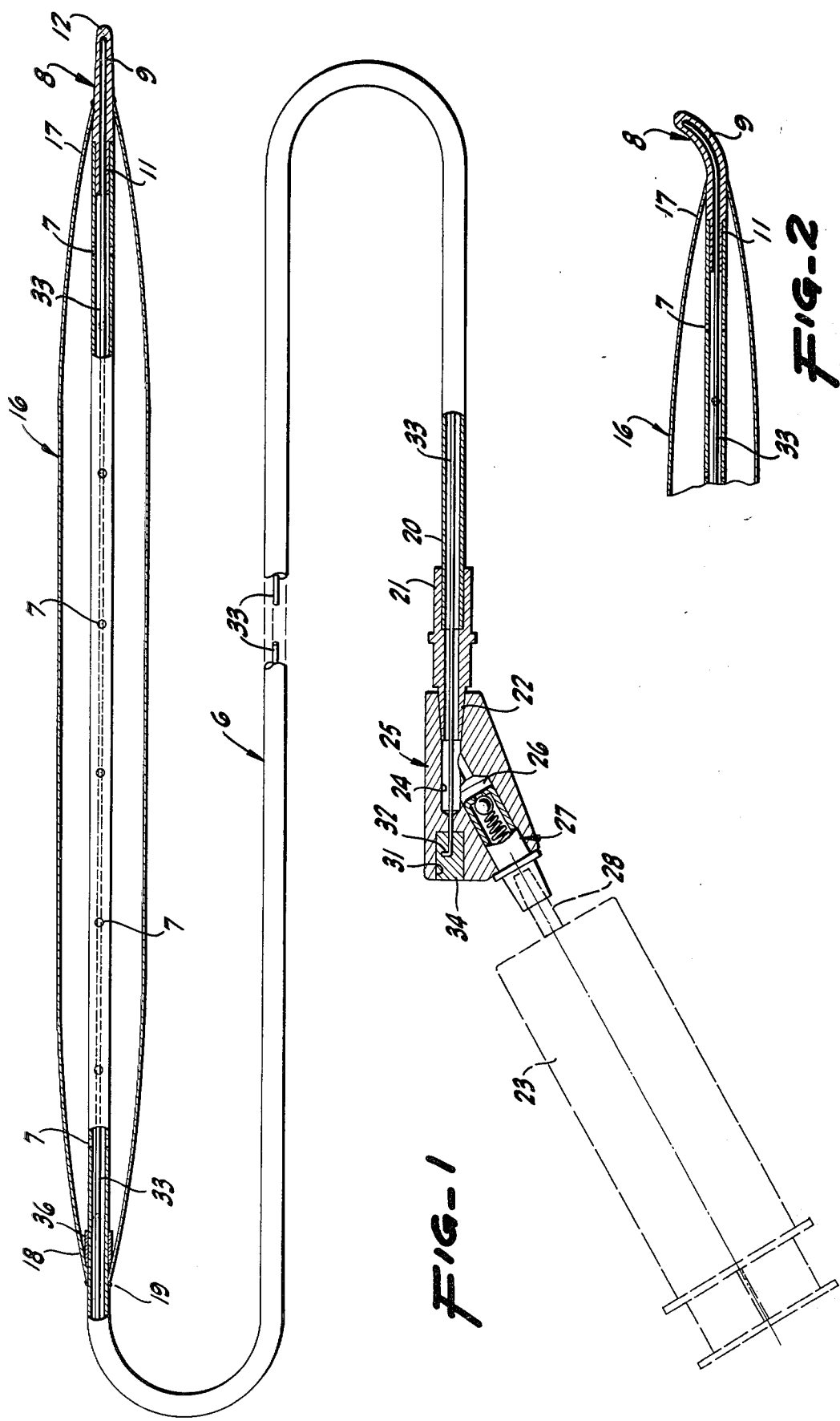

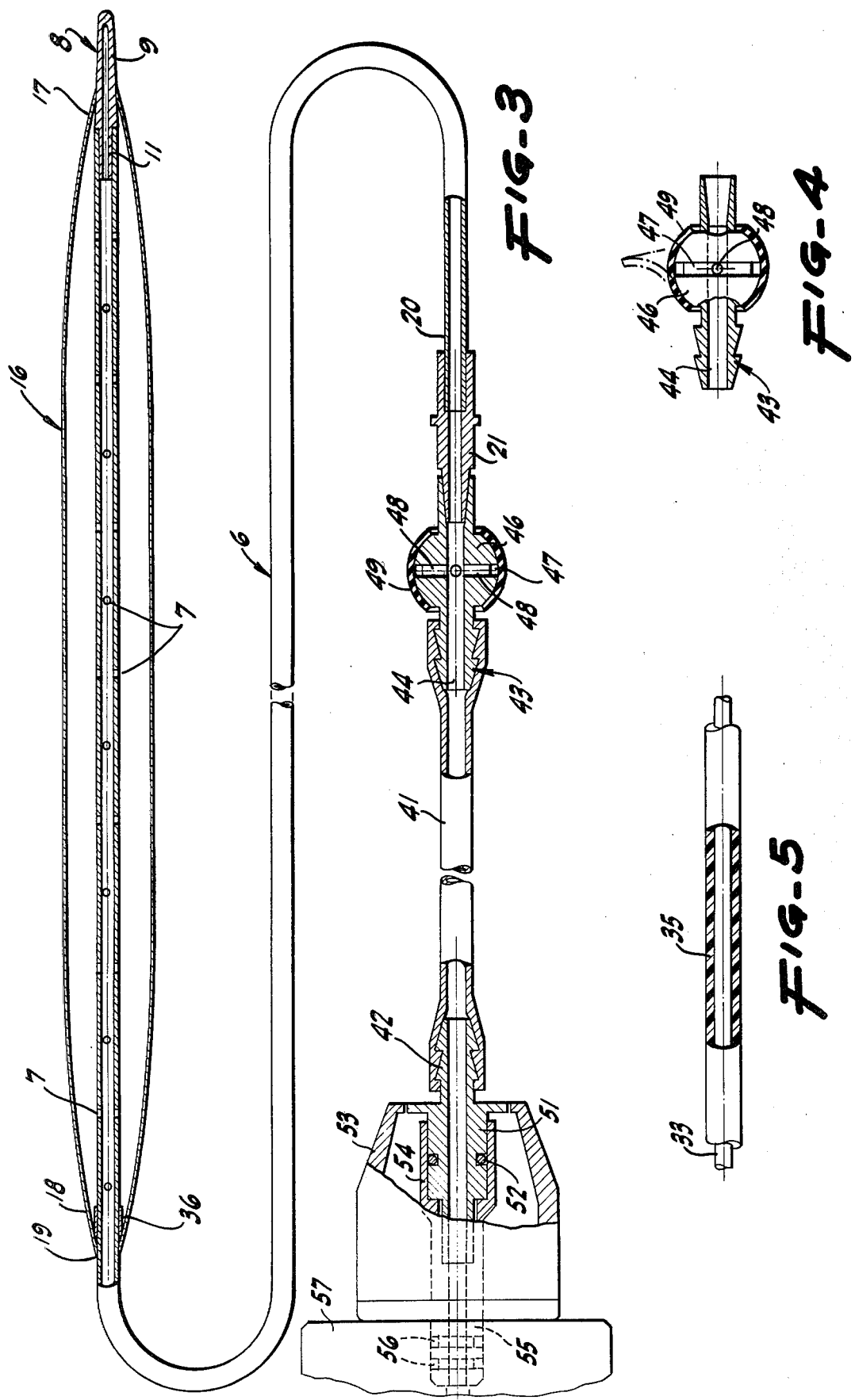

INTRA-AORTIC BALLOON

CROSS-REFERENCE TO RELATED APPLICATIONS

None, but see U.S. Pat. No. 3,769,960 of Nov. 6, 1973.

BRIEF SUMMARY OF THE INVENTION

An intra-aortic balloon has a perforated, flexible catheter at its proximal end provided with a removable connector connectable to a pump and also serving to anchor a wire extending through the catheter to a fitting at the distal end of the catheter. The wire is manually bendable. The catheter has a portion with perforations adjacent the distal end, that perforated portion being surrounded by a balloon at its ends merging with the fitting and with the catheter.

BRIEF DESCRIPTION OF THE SEVERAL VIEWS OF THE DRAWINGS

FIG. 1 is a side elevation, with portions in cross-section, of an intra-aortic balloon constructed pursuant to the invention and as it is arranged for initial installation.

FIG. 2 is a view of a portion of FIG. 1 showing a part of the free or distal end of the catheter in bent condition.

FIG. 3 is a view like FIG. 1 but showing a portion of the catheter arranged with an extension to a catheter pump and with the wire omitted.

FIG. 4 is a cross-section of a spherical portion shown in FIG. 3 but with part of a flexible band in open position.

FIG. 5 is a detail, partially in cross-section, of a Teflon armored wire.

DETAILED DESCRIPTION

While the intra-aortic balloon pursuant to the invention can be embodied in a large number of different ways all including the features of this invention, it has with success been actually embodied as shown herein. In this arrangement there is a relatively long catheter tube 6 of any suitable flexible material. For a substantial length near one end, the distal end, the catheter is provided with a number of perforations 7 through its walls to afford free access between the interior and the exterior thereof. The distal end of the catheter near the perforations is particularly closed by a fitting 8 preferably of an appropriate plastic material that is somewhat rigid but is fairly readily deformable and can be held in a deformed shape. The fitting 8 has a hollow central portion 9 and a reduced end portion 11 adapted to fit into and to be sealed within the end of the catheter itself. The other or terminus end of the fitting is appropriately reduced, closed and rounded, as at 12, for ready insertion.

Adapted to extend around the perforated, distal end of the catheter is a relatively thin-wall, flexible balloon 16 somewhat larger in the central portion than at the ends. One of the balloon ends 17 is reduced sufficiently to merge with or be permanently secured to either the end portion of the catheter itself or to the fitting 8 to form a closed junction therewith. Adjacent the other end, the balloon 16 has a reduced portion 18 which extends to, merges with or is secured to the catheter at a junction 19. Thus there is free access between the interior of the catheter 6 through the orifices 7 and the interior of the balloon 16.

Adjacent its other, proximal end 20, the catheter is permanently secured to an attachment in the form of a relatively rigid body 21 having a tapered connecting end 22. The body 21 is designed to interfit with a removable connector 25 itself joined to the stem of a standard luer syringe 23 with a tapered connecting tip. There is thus a close connection between the luer syringe 23 and the catheter 6 and the balloon 16.

Particularly pursuant to the invention, the connector 25 has an interior passage 24 that communicates with an interior duct 26. Disposed within the duct 26 is an outwardly-opening check valve assembly 27. The duct 26 is designed not only to accommodate the check valve 27, but also to receive the tapered end tube 28 or tip of the luer syringe 23. The connector 25 also has a recess 31 into which is disposed the bent end 32 of a deformable metallic wire 33 extending from a plug 34 in the connector 25 through the entire catheter tube 6 and to the far end thereof within the fitting 8. If desired, as shown in FIG. 5, the wire 33 can be armored by a Teflon jacket 35.

With this arrangement, the wire 33 can be held in position within the catheter by leaving the connector 25 in place in the attachment 21 or can be entirely withdrawn therefrom by separating the connector 25 from the attachment 21.

In order that the location of the various portions of this device can readily be ascertained, a portion of the catheter near the end of the balloon is provided with a radio-opaque ring 36 that can readily be detected by appropriate illumination.

The structure as so far described is often used by itself, but it is also sometimes supplemented with other structure as particularly shown in FIG. 3, which serves primarily as an extension and an attachment. That structure includes a tube 41 compatible with the catheter. At one end the tube 41 has an appropriate attachment 42 of a specialized nature to connect the device to a pumping structure of any of several, recognized, standard kinds.

The other end of the tube 41 is in engagement with a special fitting 43 having a bore 44 extending therethrough. In a generally spherical portion 46 of the fitting, there is a circumferential groove 47 and one or more radial passages 48 connecting the circumferential groove with the central bore 44. There is thus afforded communication between the inside of the sphere and the outside.

Since inside-outside communication normally is not needed, the spherical portion 46 is usually covered by a flexible and elastic band 49. When in position, the band prevents flow through the passages 48 to or from the atmosphere. The fitting 43 is effective to engage the male attachment 21 on the end of the catheter tube 6.

In the usual instance, this device is prepared for use in connection with a patient by first putting the syringe 23 in place on the connector 25 and also installing the connector 25 on the catheter attachment or body 21. In installing the connector 25, the wire 33 is threaded down through the entire length of the catheter 6 so as to occupy the position substantially as shown in the drawing. When this has been accomplished, the syringe 23 is actuated in order to evacuate air from the interior of the catheter and of the balloon. The pressure is so reduced as to collapse the balloon 16 closely around the body of the catheter tube 6 itself.

With the wire in position, as indicated, the operator may leave the fitting 8 in its original, axial position. But it is helpful in many instances if the operator initially manually bends the fitting 8 laterally in any desired amount, such as fifty degrees. When the operator does so, the fitting 8 stays bent because the wire retains its bent position. The bending can readily be done by finger power and often is of great assistance in permitting the operator to introduce the catheter into the patient's body and to turn and manipulate the catheter fitting 8 so that obstructions are passed. Obstructions are sometimes found in the femoral artery between the point of introduction of the device and the aorta. When the bent wire is removed, the fitting returns to its original contour. The introduction of the entire length of the catheter or as much as is desired can thus readily be accomplished.

Once the catheter tube is in its final or ultimate position, the operator then separates the connector 25 from the luer syringe 23. Thus, he may not only remove the syringe from the operation and open the interior of the catheter to atmospheric air, but may particularly detach the connector 25 and so withdraw the wire 33 from the interior of the catheter tube, leaving the catheter then unreinforced and unobstructed for its optimum use.

In many instances it occurs that the catheter should be extended. The operator may then use the mechanism shown in FIG. 3; that is, primarily the tube 41, and by introducing the male luer 21 into the fitting 43 provide a good connection for the extended distance of the tube 41.

The other end of the tube 41 engages with and over the characterized, or barbed, end of the special connector 42. This has a hollow, cylindrical body 51 with an O-ring 52 and a tapered extension all designed to be axially received directly in the corresponding receptacles in various styles of presently available, commercial drive units or consoles. Also, the body 51 can be properly received in a hollow adapter connector 53 having a close-fitting socket 54 for the body 51. In turn, the connector 53 carries some auxiliary items (not shown) within the hollow adapter connector. The socket 54 is extended to provide a hollow plug 55 that carries sealing rings 56 so as to make a proper junction with another commercial form of console receptacle 57. Thus universal connections can readily be made by using the proper hollow connector or connectors.

If at any point it is desired either to release air from the interior of the catheter tube or to permit some other gas introduction and displacement of the affected parts, the band 49 covering the apertures 48 can be peeled back. The access so afforded can be used as desired. When the band 49 is subsequently released, it returns elastically to its sealing position.

When the desired set-up is accomplished, the attachment 42 can be connected with any suitable pump or pulsor, and the operation of the catheter can continue in the regular way.

I claim:

1. An intra-aortic balloon comprising a flexible catheter having a proximal end and a distal end, means for closing said catheter at said distal end thereof, an elongated balloon having two ends, said balloon enclosing said catheter adjacent to said distal end with both of said balloon ends merging with said catheter, means establishing communication between the interior of said catheter and the surrounding interior of said balloon, a wire extending through said catheter substantially between said proximal end and said distal end thereof and movable endwise in said catheter, and a connector removably engaging the proximal end of said catheter for anchoring the proximal end of said wire to said connector.

2. A device as in claim 1 in which said means for closing said catheter at said distal end thereof is a bendable, tubular fitting having a closed distal end and an open proximate end; means for fastening the exterior of said fitting to one end of said balloon; means for telescoping said open proximal end with said catheter; and said distal end closely surrounding said wire and bendable in conformity therewith.

3. A device as in claim 1 including a body at said proximal end of said catheter and in which said connector is releasable from said body.

4. A device as in claim 3 in which said connector includes a plug, and a bent end of said wire in said plug.

* * * * *